US008071141B2

(12) United States Patent
Mae et al.

(10) Patent No.: US 8,071,141 B2
(45) Date of Patent: Dec. 6, 2011

(54) COMPOSITIONS FOR PREVENTING OR AMELIORATING MULTIPLE RISK FACTOR SYNDROMES

(75) Inventors: Tatsumasa Mae, Kakogawa (JP); Misuzu Tsukagawa, Akashi (JP); Hideyuki Kishida, Kakogawa (JP); Mitsuaki Kitano, Takasago (JP); Mikio Kitahara, Kobe (JP); Kaku Nakagawa, Kyoto (JP)

(73) Assignee: Kaneka Corporation, Kita-ku, Osaka-shi (JP)

( * ) Notice: Subject to any disclaimer, the term of this patent is extended or adjusted under 35 U.S.C. 154(b) by 0 days.

(21) Appl. No.: 11/206,073

(22) Filed: Aug. 18, 2005

(65) Prior Publication Data

US 2005/0287233 A1    Dec. 29, 2005

Related U.S. Application Data

(63) Continuation of application No. 10/433,089, filed as application No. PCT/JP01/10869 on Dec. 12, 2001, now abandoned.

(30) Foreign Application Priority Data

Dec. 12, 2000  (JP) ................................. 2000-376930
Apr. 4, 2001   (JP) ................................. 2001-106216
Jun. 25, 2001  (JP) ................................. 2001-191628

(51) Int. Cl.
*A61K 36/236*    (2006.01)
*A61K 36/00*     (2006.01)

(52) U.S. Cl. ......... 424/757; 424/725; 424/773; 514/909

(58) Field of Classification Search .................. None
See application file for complete search history.

(56) References Cited

U.S. PATENT DOCUMENTS

| 4,747,417 A | 5/1988 | Beskin |
| 4,806,365 A | 2/1989 | Nakashima |
| 4,916,066 A | 4/1990 | Akimoto et al. |
| 5,080,901 A | 1/1992 | Hangay et al. |
| 5,225,203 A | 7/1993 | Kim |
| 5,472,731 A | 12/1995 | Fuisz |
| 5,595,743 A | 1/1997 | Wu |
| 5,693,327 A | 12/1997 | Shah |

FOREIGN PATENT DOCUMENTS

| CN | 1093267 A | * | 10/1994 |
| CN | 1125134 A | * | 6/1996 |
| CN | 1269157 A | * | 10/2000 |
| EP | 0 462 022 A2 | | 12/1991 |
| EP | 1 190 717 A2 | | 3/2002 |
| JP | 1-233217 | | 9/1989 |
| JP | 1-233217 A | | 9/1989 |
| JP | 03-081227 | | 4/1991 |
| JP | 03081227 A | * | 4/1991 |
| JP | 1-175942 A | | 7/1991 |
| JP | 04-049244 | | 2/1992 |
| JP | 04297418 A | * | 10/1992 |
| JP | 5-262658 A | | 10/1993 |
| JP | 6-192086 A | | 7/1994 |
| JP | 06-263624 | * | 9/1994 |
| JP | 62-59214 | | 9/1994 |
| JP | 7-017857 A | | 1/1995 |
| JP | 07-053393 | * | 2/1995 |
| JP | 7033676 | | 2/1995 |
| JP | 07-132050 | | 5/1995 |
| JP | 7-149628 | | 6/1995 |
| JP | 7-242551 A | | 9/1995 |
| JP | 60-172926 | * | 9/1995 |
| JP | 7-309765 A | | 11/1995 |
| JP | 08-119872 | * | 5/1996 |
| JP | 8-119872 A | | 5/1996 |
| JP | 8-187066 | | 7/1996 |
| JP | 8-187066 A | | 7/1996 |
| JP | 9040572 | | 2/1997 |
| JP | 09-067264 | * | 3/1997 |
| JP | 9-067264 A | | 3/1997 |
| JP | 9-143085 A | | 6/1997 |
| JP | 9-194390 A | | 7/1997 |
| JP | 10-130161 A | | 5/1998 |
| JP | 10-265328 A | | 10/1998 |
| JP | 11130686 A | * | 5/1999 |
| JP | 11-187843 A | | 7/1999 |
| JP | 11-246398 | | 9/1999 |
| JP | 11-246399 | | 9/1999 |
| JP | 11-246399 A | | 9/1999 |
| JP | 11243913 | | 9/1999 |
| JP | 10-231495 A | | 10/1999 |
| JP | 2000-044484 | * | 2/2000 |
| JP | 2000-44484 A | | 2/2000 |
| JP | 2000-72682 A | | 3/2000 |
| JP | 2000-302633 A | | 10/2000 |
| JP | 2000-319191 A | | 11/2000 |
| JP | 2001-064192 | | 3/2001 |
| JP | 2001-120237 A | | 5/2001 |
| JP | 2001-139466 | | 5/2001 |
| JP | 2000-144170 A | | 6/2001 |
| JP | 2002-114695 | | 4/2002 |
| WO | WO 9742928 | * | 11/1997 |
| WO | WO 99/22752 | | 5/1999 |

OTHER PUBLICATIONS

JP 08-119872 (Kikuchi et al) May 14, 1996 (Machine translation) [online] [retrieved on Apr. 11, 2007]. Retrieved from the Internet: <http://www19.ipdl.inpit.go.jp/PA1/cgi-bin/PA1INDEX>.*

(Continued)

*Primary Examiner* — Qiuwen Mi

(74) *Attorney, Agent, or Firm* — Connolly Bove Lodge & Hutz LLP

(57) ABSTRACT

A composition for preventing or ameliorating multiple risk factor syndrome involving visceral fat-type obesity, diabetes mellitus, hyperlipemia and hypertension, which comprises at least one member selected from the group consisting of a licorice hydrophobic extract, a turmeric extract, a clove extract, and a cinnamon extract.

16 Claims, No Drawings

OTHER PUBLICATIONS

JP 06-263624 (Hara) Sep. 20, 1994 (Machine translation) [online] [retrieved on Apr. 10, 2007]. Retrieved from the Internet: <http://www19.ipdl.inpit.go.jp/PA1/cgi-bin/PA1INDEX>.*

JP 09-067264 (Fukuda et al) Mar. 11, 1997 (Machine translation) [online] [retrieved on Apr. 11, 2007]. Retrieved from the Internet: <http://www19.ipdl.inpit.go.jp/PA1/cgi-bin/PA1INDEX>.*

JP 07-053393 (Kitada et al) Feb. 28, 1995 (Machine translation) [online] [retrieved on Apr. 11, 2007]. Retrieved from the Internet: <http://www19.ipdl.inpit.go.jp/PA1/cgi-bin/PA1INDEX>.*

JP 60-172926 (Noma) Sep. 6, 1985 (Abstract only, Machine Translation not available) [online] [retrieved on Apr. 10, 2007]. Retrieved from the Internet: <http://www19.ipdl.inpit.go.jp/PA1/cgi-bin/PA1INDEX>.*

JP 2000-044484 (Murata et al) Feb. 15, 2000 (Machine translation) [online] [retrieved on Apr. 11, 2007]. Retrieved from the Internet: <http://www19.ipdl.inpit.go.jp/PA1/cgi-bin/PA1INDEX>.*

Queiroz et al, Association between Helicobacter and gastric ulcer disease of the pars esophagea in swine. Gastroenterology. Jul. 1996; 111(1): 19-27.*

Perel et al, Comparison of treatments between animal experiments and clinical trials: systematic review. BMJ, doi: 10.1136/bmj.39048.407928.BE (published Dec. 15, 2006).*

Kahn et al, The metabolic syndrome: time for a critical appraisal. Diabetologia (2005) 48: 1684-1699.*

Jensen, Health consequences of fat distribution, Hormone research, 1997; 48 (suppl 5): 88-92.*

Tarui et al, Visceral fat obesity: anthropological and pathophysiological aspects, International journal of obesity, (Sep. 1991) vol. 15 Suppl 2, pp. 1-8.*

Sobotka et al, Neuro behavioral toxicity of ammoniated glycyrrhizin a licorice component in rats, Neurobehavioral Toxicology and Teratology, (1981) vol. 3, No. 1, pp. 37-44.*

Kobayashi, Hyperlipidemia in subjects with obesity, Complication—Tonyobyo to Kekkan (1999), 4(1), 93-100.*

Jin-Ichi Inokuchi, et al., Inhibitors of Angiotensin Converting Enzyme in Crude Drugs. I, *Chem. Pharm. Bull.*, 1984, vol. 32, No. 9, pp. 3615-3619.

Summary of Kanzo (Glycyrrhiza uralensis), Antiarteriosclerotic activity of glycyrrhizin and its mechanism, *Chiryogaku*, 1985, vol. 14, No. 1, pp. 127-134.

Patent Abstract of Japan, XP-002272664, Sarhad Journal of Agriculture, 1994.

Patent Abstract of Japan, JP-01233217; Tsumura & Co., Sep. 19, 1989.

Preuss H.G., "Use of Natural Supplements for Syndrome X", Journal of the American College of Nutrition, 19(5) 696 (2000) (abstract).

Matsuzawa, Yuji, "Pathophysiology and Molecular Mechanisms of Visceral Fat Syndrome: The Japanese Experience", *Diabetes/Metabolism Reviews*, vol. 13, No. 1, 1997, pp. 3-13.

Reaven, Gerald M., "Role of Insulin Resistance in Human Disease", *Diabetes*, vol. 37, Dec. 1988, pp. 1595-1607.

Kaplan, Normal M., MD, "The Deadly Quartet, Upper-Body Obesity, Glucose Intolerance, Hypertriglyceridemia, and Hypertension", *Arch. Intern. Medicine*, vol. 149, Jul. 1989, pp. 1514-1520.

Yasuko Shiki et al., "Influence of cinnamic acid on very low-density lipoprotein synthesis", Therapeutic Research, vol. 2, No. 6, 1985, p. 1092-1097.

Third Party Observation in counterpart Japanese application No. JP2002-549269, Nov. 21, 2006.

Jahromi et al., Journal of Natural Products, 1993, vol. 56. No. 7, pp. 989-994.

Takii et al., Bioscience Biotechnology and Biochemistry, 1997, vol. 61, No. 9, pp. 1531-1535.

Office Action for CN 01820494.5, Aug. 1, 2008.

Office Action for JP 2002-549269, Sep. 16, 2008.

International Preliminary Examination Report issued in corresponding International Application No. PCT/ JP01/10869 submitted on Oct. 9, 2003.

Broadhurst et al., Insulin-like Biological Activity of Culinary and Medicinal Plant Aqueous Extracts in Vitro, J. Agric. Food Chem., vol. 48, No. 3, 2000, pp. 849-852.

Sekiya et al., Effect of medicinal plants on preadipocyte differentiation, Journal of Traditional Medicines, 1997, vol. 14, No. 4, pp. 356-357.

"Examination of the technique in production of high quality chickens and eggs", Ibaraki-ken Yokeishikenjo Kenkyuhokoku, vol. 27, 1993, pp. 12-14.

Ilaaj-al-Amraaz, (18th century AD), Afzal-al-Matabe, Barqi Press, Delhi, 1921 AD p. 236.

Athmarakshaamirtham, Pub: Ilakkana Achagam, chennai (1879) p. 534.

Bayaaz-e-Kabir, vol. II (Compiled), Daftar-al-Maseeh, Karol Bagh, New Delhi, 1938 AD p. 173-174.

Ilaaj-al-Amraaz (18th century AD), Afzal-al-Matabe, Barqi Press, Delhi, 1921 AD p. 183.

Qaraabaadeen Azam wa Akmal (20th century AD), Matba Siddiqi, Delhi/Matba Mustafai, Delhi, 1909 AD p. 581.

Agathiyar vaithya vallathi 600, Pub & Ed Deenadhayalu muthaliar, Chennai, (1924) p. 138, 139.

Qaraabaadeen Qaadri (17th century AD), Ahmadi Publication, Delhi, 1968 AD p. 153.

Details of Prior art in languages—Persian, Urdu and Tamil with Translation in CIPO Official Language in relation Publication No. WO 2002/047699, 2002.

International Preliminary Examination Report issued in corresponding International Application No. PCT/ JP01/10869 submitted on Oct. 9, 2003.

* cited by examiner

COMPOSITIONS FOR PREVENTING OR AMELIORATING MULTIPLE RISK FACTOR SYNDROMES

This is a continuation of application Ser. No. 10/433,089 filed 11 Sep. 2003 now abandoned, which is a 371 of PCT/JP01/10869 filed 12 Dec. 2001, claiming priority to JP 2000-376930 filed 12 Dec. 2000, JP 2001-106216 filed 4 Apr. 2001, and JP 2001-191628 filed 25 Jun. 2001, the contents of which are incorporated herein by reference.

TECHNICAL FIELD

The present invention relates to a composition for preventing or ameliorating multiple risk factor syndrome involving visceral fat-type obesity, diabetes mellitus, hyperlipemia and hypertension.

BACKGROUND ART

Lifestyle-related disease arising from deteriorations of living habit such as supernutrition and underexercise is a major social concern today. Lifestyle-related disease involves various states of disease such as obesity, diabetes mellitus, hyperlipemia and hypertension, and these states of disease are gathering considerable attention as multiple risk factor syndrome that may be an underlying disease of arteriosclerosis. Moreover, this is a matter of concern not only in humans but also in pet animals such as dogs and cats.

Obesity is roughly classified into subcutaneous fat-type obesity resulting from accumulation of subcutaneous fat and visceral fat-type obesity resulting from accumulation of intra-abdominal fat.

Visceral fat-type obesity is a disease which is accompanied by hyperlipemia, glucose tolerance abnormality, and hypertension at high rates and also characterized by strong insulin resistance so that it is known as multiple risk factor syndrome. Moreover, visceral fat accumulation is not only found in obese individuals but also observed in persons within the normal body weight range and is likely to accompany the multiple risk referred to above (BIO Clinica, September, 2000 expanded issue, 16-55). This, visceral fat accumulation triggers insulin resistance, diabetes mellitus, hyperlipemia, hypertension and the like. Matsuzawa et al. coined the term "visceral fat syndrome" for this disease entity (Diabetes/Metabolism Reviews, 13, 3-13, 1997). "Syndrome X" as proposed by G. M. Reaven (Diabetes, 37, 1595-1607, 1988), "deadly quartet" as proposed by N. M. Kaplan (Archives of Internal Medicine, 149, 1514-1520, 1989), and "insulin-resistance syndrome" as proposed by R. A. DeFronzo (Diabetes Care, 14, 173-194, 1991) signify the same disease entity.

The therapy of obesity generally consists of diet therapy and exercise therapy, and drug therapy is indicated in serious obesity cases. However, these therapeutic regimens are recommended or prescribed to patients by medical institutions, and are not directed to the so-called candidate patients in the reserve. Moreover, appetite suppressants, inhibitors of digestion and absorption of carbohydrate and fat as energy sources, and energy consumption promoters can be mentioned as anti-obesity agents. However, appetite suppressants and inhibitors of digestion and absorption do not positively lower visceral fat, and energy consumption promoters do not specifically lower visceral fat.

Japanese Kokai Publication Hei-11-187843 discloses that administration of an extract of *Cassia nomame* having fat absorption inhibitory action and an extract of *Morus bombycis* having carbohydrate absorption inhibitory action in combination leads to inhibition of body weight gain and reductions in subcutaneous fat and visceral fat. Regarding other substances of the natural origin, it is known that substances derived from highly unsaturated oils such as fish oil and vegetable oil, e.g. linseed oil and perilla oil (Japanese Kokai Publication Hei-10-231495), or conjugated isomerized highly unsaturated fatty acids (Japanese Kokai Publication 2000-144170) have an accumulated visceral fat lowering function, that an amylase inhibitor derived from wheat (Japanese Kokai Publication Hei-09-194390) inhibits visceral fat accumulation, and that D-xylose and/or L-arabinose (Japanese Kokai Publication Hei-07-309765 and Japanese Kokai Publication Hei-07-242551) inhibits accumulation of body fat (subcutaneous fat and visceral fat).

Diabetes mellitus is a disease the chief manifestation of which is chronic hyperglycemia resulting from a deficiency in insulin activity, and not less than 90% of diabetics are those with type II diabetes (non-insulin dependent diabetes mellitus; NIDDM). The number of diabetic patients in Japan has increased dramatically from 1.57 million in 1993 to 2.18 million in 1996 (a patient survey of the Health and Welfare Ministry). Furthermore, according to the Health and Welfare Ministry's diabetes census undertaken in November 1997, the persons strongly suspected to be diabetic (inclusive of those on therapy) numbered 6.9 million and the sum of this number and the number of individuals in whom diabetes could not be ruled out was estimated at 13.7 million. Thus, besides the sharply increasing number of diabetics, the number of individuals in the reserve and not on therapy by medical institutions is by far large, and this is a matter of serious concern.

The therapy of diabetes mellitus includes diet therapy and exercise therapy, and in cases not sufficiently responsive to these therapies, drug therapy is superimposed. The drug therapy includes insulin therapy and administration of oral hypoglycemic drugs. As oral hypoglycemic drugs, there can be mentioned sulfonylurea derivatives such as tolbutamide and glibenclamide; biguanides such as buformin and metformin; α-glucosidase inhibitors such as acarbose and voglibose; and insulin resistance improving drugs such as troglitazone and pioglitazone.

In diet therapy, the patient is recommended to refrain from overeating and adhere to a legitimate calorie intake and, if one is obese, instructed to make efforts to slim down to the standard body weight. As foodstuffs to be used in diet therapy, assorted foods for preparation of diets for diabetics, which are special-use foods approved by the Health and Welfare Ministry, are known. However, these are no more than the so-called low-calorie, balanced-nutrition foods, and cannot be considered to have intrinsic therapeutic efficacy for diabetes.

Furthermore, these therapies are prescribed for diabetics by medical institutions and not directed to the so-called diabetics in the reserve who outnumber the diabetics by a large margin. There is accordingly a demand for a composition effective for preventing or ameliorating diabetes mellitus in the form of a food/beverage, such as food with health claims (food for specified health uses and food with nutrient function claims) or health food, or a drug (inclusive of a quasi-drug) to which access may be easily had by any one not associated with medical institutions.

The incidence of diabetes has been on the steady increase in domestic or pet animals, too, and development of a composition effective for preventing or ameliorating diabetes in domestic and pet animals is being desired.

Japanese Kokai Publication Hei-01-233217 discloses an antidiabetic composition comprising curcumenone, the extract of *Curcuma aromatica*, the family Zingiberaceae, as an active ingredient. Japanese Patent Hei-06-192086 discloses an antidiabetic composition comprising (4S,5S)-(+)-germacrone-4,5-epoxide, the extract of *Curcuma aromatica*, as an active ingredient. *Curcuma aromatica* is known to be a crude drug but has not been cleared for use as a food additive.

Licorice and its aqueous extract are in use as crude drugs having analgesic/anticonvulsant and expectorant actions or as foods. Since the chief component glycyrrhizin (glycyrrhizinic acid) is about 200 times as sweet as sucrose, the "licorice extract" obtainable by extracting licorice with water or an alkaline aqueous medium is a food additive for use as a sweetener as well (Annotated List of Additives in Available Books, page 163, Japanese Food Additives Association, 1999). Its physiologic actions so far known are adrenocortical electrolyte or glycocorticoid-like action, estrogen-like action, testosteron production-inhibitory action, antitussive action, antiinflammatory action, antiallergic action, detoxicating action, hyperlipemia-improving action, gastric mucosal cell cyclic-AMP concentration increasing action, experimental liver impairment preventing or ameliorating action, antiviral action, interferon-inducing action, anticaries action, tumor promoter inhibitory action, cytosolic $Ca^{2+}$ lowering action, phospholipase $A_2$ inhibitory action, $LTB_4$ and $PGE_2$ production inhibitory action, and platelet activating factor production inhibitory action, among others. Furthermore, licorice is one of the components of the traditional Chinese medicine Byakko-ka-Ninjin-To which is prescribed for the diabetes-associated intense dry-mouth, polyposia, and polyuria and, like gypsum, anemarrhena, and ginseng which are also formulated, an aqueous extract of licorice reportedly has a hypoglycemic action (I. Kimura, et al.: Phytotheraphy Research, 13, 484-488, 1999).

The licorice residues which remain after extraction of glycyrrhizin from licorice with water or an aqueous alkaline medium are known to have a hepato-tonic (hepatoprotectant) action and/or an antiinfective action (Japanese Kokai Publication Hei-09-143085), an immunopotentiating action (Japanese Kokai Publication Hei-05-262658), and an antiviral action (Japanese Kokai Publication Hei-01-175942). Furthermore, the "licorice oily extract" which can be obtained by extracting the residues of licorice after aqueous washing with ethanol, acetone, or hexane is an antioxidant for use as a food additive (Annotated Lists of Additives in Available Books, page 164, Japanese Food Additives Association, 1999). The licorice oily extract is known to have antibacterial activity against *Helicobacter pylori* (Japanese Kokai Publication Hei-10-130161, Japanese Kokai Publication Hei-08-119872). However, it is not known that said licorice residues after extraction of glycyrrhizin or said licorice oily extract ever has a visceral fat lowering action, a hypoglycemic action, a lipid metabolism improving action, or a blood pressure elevation inhibitory action.

Incidentally, it is long known that an excessive intake or prolonged use of licorice induces pseudoaldosteronism inclusive of hypertension, edema, and hypokalemia. This condition is caused by glycyrrhizin which is the main component of licorice. It is also reported that hypertension may be elicited by glycyrrhetinic acid which is a hydrolyzate of glycyrrhizin (H. Siguruonsdottir, et al.: Journal of Human Hypertension, 15, 549-552, 2001). Thus, a licorice aqueous extract which contains the hydrophilic fraction of licorice and is composed predominantly of glycyrrhizin induces hypertension.

As tropical plants relegated to the genus *Curcuma*, the family Zingiberaceae, of Tropical Asian origin, several varieties such as *Curcuma longa, Curcuma aromatica, Curcuma zedoaria*, and *Curcuma xanthorrhiza* are known. Among these, *Curcuma longa* is commonly called "turmeric" and known to be one of the component spices of curry. This is not only used as a foodstuff but, because the principal component curcumin of *Curcuma longa* is a yellow dye (natural color), this plant or an extract thereof (curcuma dye) is used as a dyestuff or a coloring agent (a food additive). As a herbal medicine in traditional therapies such as Kampo (traditional Chinese medicine) of China, Ayur-Veda of India, and Jamu of Indonesia, it is long known that *Curcuma longa* has hemostatic, stomachic, antibacterial, and antiinflammatory actions, and actually this plant is still in use as a medicine. Furthermore, the efficacy of turmeric (*Curcuma longa*) and its principal component curcumin is attracting attention and has been found to have various physiologic actions such as an antioxidant action, a cholagogue action (a choleretic action), a visceral (liver, pancreas) function-potentiating action, an anti-tumor effect, a lipid metabolism improving action, and a skin lightening action.

However, it is not known that turmeric or its extract ever has a visceral fat lowering action, a hypoglycemic action, or a blood pressure elevation inhibitory action.

Clove is the flower-bud, leaf, or flower of *Syzygium aromaticum* or *Eugenia caryophyllata* of the family Myrtaceae and is known to be one of spices. By virtue of its antibacterial/bactericidal action and an analgesic/anesthetic action, clove has been used for many generations not only as a breath sweetener or an antiodontalgic but also as a stomachic in the realm of crude drugs and herbal medicines (Kampo medicine). Furthermore, a clove extract has been applied as an antioxidant for food additive use. However, it is not known that clove or its extract ever has visceral fat lowering action, a hypoglycemic action, a lipid metabolism improving action or a blood pressure elevation inhibitory action.

Cinnamon or cassia is the bark of *Cinnamomum cassia, C. zeylanicum*, or *C. loureirii* of the family Lauraceae. Cinnamon has antibacterial and antioxidant actions and has long been used as one of spices and its bark has been used in medicinal applications. However, it is not known that cinnamon or its extract has a visceral fat lowering action, a hypoglycemic action, a lipid metabolism improving action, or a blood pressure elevation inhibitory action.

SUMMARY OF THE INVENTION

The present invention has for its object to provide a composition for preventing or ameliorating multiple risk factor syndrome involving visceral fat-type obesity, diabetes mellitus, hyperlipemia, and hypertension, without risks for side effects or other safety problems.

The inventors of the present invention, postulating that the cause of multiple risk factor syndrome is visceral fat-type obesity, considered that multiple risk factor syndrome can be prevented or ameliorated by lowering accumulated visceral fat.

Therefore, the inventors explored in earnest for possible means for accomplishing the above object and found that a licorice hydrophobic extract, a turmeric extract, a clove extract, and a cinnamon extract each has an accumulated visceral fat lowering action, a blood glucose elevation inhibitory action, a hypoglycemic action, a lipid metabolism improving action and a blood pressure elevation inhibitory action. The present invention has been developed on the basis of the above finding.

The present invention, therefore, is directed to a composition for preventing or ameliorating multiple risk factor syndrome which comprises at least one member selected from the group consisting of a licorice hydrophobic extract, a turmeric extract, a clove extract, and a cinnamon extract. This composition for preventing or ameliorating multiple risk factor syndrome according to the invention may be a composition for preventing or ameliorating visceral fat-type obesity, a composition for preventing or ameliorating diabetes mellitus, a composition for preventing or ameliorating hyperlipemia, or a composition for preventing or ameliorating hypertension.

The present invention is further directed to a method for preventing or ameliorating multiple risk factor syndrome which comprises administering or applying a composition containing at least one member selected from the group consisting of a licorice hydrophobic extract, a turmeric (*Curcuma longa*) extract, a clove extract, and a cinnamon extract to a human being, a domestic animal, or a pet animal.

Furthermore, the present invention is directed to the use of at least one member selected from the group consisting of a licorice hydrophobic extract, a turmeric extract, a clove extract, and a cinnamon extract for the production of a composition for preventing or ameliorating multiple risk factor syndrome.

DETAILED DESCRIPTION OF THE INVENTION

The present invention is now described in detail.

The composition of the present invention comprises at least one member selected from the group consisting of a licorice hydrophobic extract, a turmeric extract, a clove extract, and a cinnamon extract. These extracts are food items and, moreover, have been cleared for use as food additives, thus being free from side effects and other safety problems.

The composition of the invention has a visceral fat lowering action and, as such, is capable of preventing or ameliorating multiple risk factor syndrome, hence, visceral fat-type obesity, diabetes mellitus, hyperlipemia, and hypertension. Thus, in addition to said visceral fat lowering action, it has a blood glucose elevation inhibitory action, a hypoglycemic action, a lipid metabolism improving action, and a blood pressure elevation inhibitory action. The lipid metabolism improving action mentioned just above is a total cholesterol lowering action, a triglyceride lowering action, or a free fatty acid lowering action in serum.

The diabetes mellitus in multiple risk factor syndrome is type II diabetes (non-insulin dependent diabetes mellitus) resulting from glucose tolerance abnormality. Moreover, the hyperlipemia in multiple risk factor syndrome is a state of disease characterized by an elevation of serum total cholesterol, triglyceride, or free fatty acid resulting from an abnormality of lipid metabolism.

The visceral fat lowering effect can be titrated by weighing the accumulated intra-abdominal fat, for example the fat around the genital organ (epididymis, uterus), perirenal fat, mesenteric fat, omental fat, etc. in experimental animals. The experimental animals for use in this procedure are preferably dietary obesity model animals reared on a high-fat diet (M. Rebuffe-Scrive, et al., Metabolism, 42, 1405-1409, 1993) or hereditary obesity model animals, such as KK mice, KK-Ay mice, ob/ob mice, db/db mice, Zucker fatty rats, and OLETF rats. The visceral fat lowering effect can be evaluated from a reduction in the visceral fat area on an abdominal CT scan image in experimental animals (C. S. Hun, et al.: Biochemical and Biophysical Research Communications, 259, 85-90, 1999) and humans (K. Tokunaga, et al.: International Journal of Obesity, 7, 437-445, 1983) but more expediently from a reduction in the girth.

Furthermore, because the composition of the invention has a visceral fat lowering action, it is capable of preventing or ameliorating multiple risk factor syndrome involving visceral fat-type obesity, diabetes mellitus, hyperlipemia, and hypertension. Thus, by lowering visceral fat, the body fat percentage can be decreased to prevent or ameliorate obesity. Moreover, as visceral fat is decreased, the amounts of secretion of various physiologically active substances (adipocytokines) from adipocytes, such as leptin, TNF-$\alpha$ (tumor necrosis factor-$\alpha$), free fatty acids, apoprotein E, angiotensinogen, PAI-1 (plasminogen activator inhibitor-1), etc. are decreased. Thus, as visceral fat is decreased, TNF-$\alpha$ involved in insulin resistance is decreased and the blood glucose level is depressed by the resulting improvement in insulin resistance and remission of glucose tolerance impairment, thus contributing to preventing or ameliorating diabetes mellitus. Moreover, as free fatty acids and apoprotein E, which is associated with lipid transport, are decreased, lipid abnormalities are ameliorated to depress the blood lipid level, thus contributing to preventing or ameliorating hyperlipemia. Angiotensinogen, which is involved in the regulation of blood pressure, and PAI-1, which is involved in thrombus formation, are also decreased and the blood pressure falls, contributing to preventing or ameliorating hypertension or arteriosclerosis.

Licorice, the raw material of the licorice hydrophobic extract for use in the present invention, includes *Glycyrrhiza glabra*, *G. uralensis*, and *G. inflata*, of the genus *Glycyrrhiza*, the family Leguminosae. Licorice is a food eaten over centuries, and has been used as a food additive and a crude drug as well.

The licorice hydrophobic extract for use in the invention can be obtained by extracting the active component of licorice or its powder with an organic solvent. An alternative production process comprises extracting out the hydrophilic component of licorice with water or an alkaline aqueous solution in advance and extracting the licorice residue, either as it is or after drying, with an organic solvent. The organic solvent for use in this process is preferably a solvent that has been cleared for use in the production and processing of pharmaceutical products, foods, and food additives, thus including acetone, ethanol, gycerol, ethyl acetate, diethyl ether, cyclohexane, butanol, propanol, propylene glycol, hexane, and methanol, among others. Oils such as edible oils can also be used. A mixture of two or more kinds of such solvents and a mixture of any of them with water may also be used. Furthermore, in order to extract out the hydrophobic fraction of licorice using a single solvent with good efficiency, ethyl acetate, acetone or ethanol is preferred. The extract obtained by extracting out the hydrophobic fraction of licorice or the extract from which the extractant solvent has been removed is herein defined as the licorice hydrophobic extract. Moreover, unless it contains impurities objectionable in pharmaceutical products and foods, a crude extract or a semi-purified extract can also be used in the present invention.

Turmeric, the raw material of the turmeric extract for use in the present invention, is the root or the rhizome of *Curcuma longa* which is a perennial plant of the genus *Curcuma*, the family Zingiberaceae. Turmeric is a food eaten over centuries as the spice "turmeric", and turmeric dye obtainable by extracting turmeric with an organic solvent, such as ethanol, hexane, or acetone, has been cleared for use as a food additive for coloring and ranks high in safety.

The turmeric extract for use in the invention can be obtained by extracting the active component of turmeric or its powder with water or an organic solvent. The organic solvent for use in this process is preferably a solvent that has been cleared for use in the production and processing of pharmaceutical products, foods and food additives, thus including, acetone, ethanol, glycerol, ethyl acetate, diethyl ether, cyclohexane, butanol, propanol, propylene glycol, hexane, methanol, among others. Oils such as edible oils can also be used. A mixture of two or more kinds of such solvents and a mixture of any of them with water may also be used. The extract obtained by the above extraction procedure or the extract from which the extractant solvent has been removed is herein defined as the turmeric extract. Moreover, unless it contains impurities objectionable in pharmaceutical products and foods, a crude extract or a semi-purified extract can also be used in the present invention.

Clove, the raw material of the clove extract for use in the present invention is the flower-bud, leaf, or flower of *Syzygium aromaticum* or *Eugenia caryophyllata* of the family Myrtaceae. Clove is a food eaten over centuries as a spice, and the clove extract has been cleared for use as a food additive functioning as an antioxidant and ranks high in safety.

The clove extract for use in the invention can be obtained by extracting the active component of clove or its powder with water or an organic solvent. The organic solvent for use in this process is preferably a solvent that has been cleared for use in the production and processing of pharmaceutical products, foods and food additives, thus including, acetone, ethanol, glycerol, ethyl acetate, diethyl ether, cyclohexane, butanol, propanol, propylene glycol, hexane, methanol, among others. Oils such as edible oils can also be used. Among these solvents, two or more species may be used as a mixture or a mixture thereof with water may also be used. The extract obtained by the above extraction procedure or the extract from which the extractant solvent has been removed is herein defined as the clove extract. Moreover, unless it contains impurities objectionable in pharmaceutical products and foods, a crude extract or a semi-purified extract can also be used in the present invention.

Cinnamon, the raw material of the cinnamon extract for use in the invention is *Cinnamomum cassia, C. zeylanicum,* or *C. loureirii* of the genus *Cinnamomum* of the family Lauraceae. Cinnamon is a food eaten over centuries as a spice and has no side effect or other safety problem.

The cinnamon extract for use in the invention can be obtained by extracting the active component of cinnamon or its powder with water or an organic solvent. The organic solvent for use in this process is preferably a solvent that has been cleared for use in the production and processing of pharmaceutical products, foods and food additives, thus including, acetone, ethanol, glycerol, ethyl acetate, diethyl ether, cyclohexane, butanol, propanol, propylene glycol, hexane, methanol, among others. Oils such as edible oils can also be used. Among these solvents, two or more species may be used as a mixture or a mixture thereof with water may also be used. The extract obtained by the above extraction procedure or the extract from which the extractant solvent has been removed is herein defined as the cinnamon extract. Moreover, unless it contains impurities objectionable in pharmaceutical products and foods, a crude extract or a semi-purified extract can also be used in the present invention.

The composition of the invention is a composition for preventing or ameliorating multiple risk factor syndrome and provided that it contains at least one member of the group consisting of said licorice hydrophobic extract, turmeric extract, clove extract, and cinnamon extract, it is not restricted in form and can be used as a food/beverage, such as food with health claims (food for specified health uses and food with nutrient function claims) or health food, or as a pharmaceutical product, a cosmetic product, or a quasi-drug.

For use as a food/beverage, it can be directly ingested or may be formulated into easily ingestable products, such as capsules, tablets, granules, and the like, with the aid of a known carrier, auxiliary agent or the like for ingestion. The amount of each extract in such a formulated product may be 0.1 to 100 weight %, preferably 10 to 90 weight %. Furthermore, it can be mixed into raw materials for all kinds of food and beverage products, for example confections such as chewing gum, chocolate, candies, jellies, biscuits, crackers, etc.; frozen sweets such as ice cream, ice candies, etc.; beverages such as tea, nonalcoholic beverages, nutritional drinks, drinks for beauty, etc.; noodles such as Japanese wheat noodles, Chinese noodles, spaghetti, instant noodles, etc.; fish paste foods such as fish minced and steamed (kamaboko), fish sausage (chikuwa), minced flesh (hannpen), etc.; seasonings such as dressings, mayonnaise, sauces, etc.; oleaginous products such as margarine, butter, salad oil, etc.; bakery products, hams, soups, retort foods, frozen foods, and so forth. In taking such a food or beverage composition, the recommended daily intake for an adult human is 0.1 to 1,000 mg/kg, more preferably 1 to 100 mg/kg, on an extract content basis. Such compositions can also be used as feeds for domestic and pet animals or as pet foods, and the recommended daily intake in these applications is preferably 0.1 to 1,000 mg/kg on an extract content basis.

For use as a pharmaceutical product, the dosage form is not particularly restricted but includes capsules, tablets, granules, injections, suppositories, and patches. Such dosage forms can be prepared by suitably formulating pharmaceutically acceptable material for preparation such as excipient, disintegrator, lubricant, binder, antioxidant, coloring agent, aggregation inhibitor, absorption promoter, solubilizing agent, stabilizer, and so on. The daily dosage of such a preparation for adult human is 0.1 to 1,000 mg/kg, preferably 1 to 100 mg/kg, on an extract content basis, which dosage is to be administered once a day or in a few divided doses a day. The composition can also be used as a pharmaceutical product for domestic and pet animals and the daily dosage for this application is preferably 0.1 to 1,000 mg/kg on an extract content basis.

For use as a cosmetic agent or a quasi-drug, the composition can be used in such forms as, inter alia, ointments, liniments, aerosols, creams, soaps, face cleansers, body cleansers, toilet water, lotions, and bath agents.

The composition of the invention can be administered or applied to all animals inclusive of fish, reptiles, amphibians, feathers, and mammals. The mammalian animal referred to just above is not particularly restricted but includes human, monkeys, dogs, cats, bovine species, equine species, swine species, sheep, mice, rats, and guinea pigs, among others.

BEST MODE FOR CARRYING OUT THE INVENTION

The following examples illustrate the present invention in further detail without defining the scope of the invention.

Licorice Hydrophobic Extract

PREPARATION EXAMPLE 1

Preparation of a Licorice Hydrophobic Extract-1

Using a glass vessel, 500 g of licorice powder (Kaneka Sun Spice Co., Ltd.) was steeped in 5 volumes of ethyl acetate and allowed to stand at room temperature, protected against light, for 1 week with occasional stirring. The mixture was filtered through filter paper (ADVANTEC No. 2) twice to remove the powder and recover an extract solution. The extract solution was concentrated under reduced pressure to remove the solvent, whereupon 33.91 g of a licorice hydrophobic extract was obtained.

REFERENCE EXAMPLE 1

The Glycyrrhizin Content of the Licorice Hydrophobic Extract

The glycyrrhizin content of the licorice hydrophobic extract prepared in Preparation Example 1 was quantitated by HPLC referring to the method of M. A. Raggi, et al. (Boll. Chim. Farmaceutico., 133, 704-708, 1994). As the analytical column, COSMOSIL 5C18-AR, 4.6×250 mm (Nacalai Tesque, Inc.) was used at 40° C. Using acetonitrile:distilled water:acetic acid (35:65:0.5, v/v) as a mobile phase run at a flow rate of 1 ml/min., the peak was detected at 251 nm. Using ammonium glycyrrhizinate (Wako Pure Chemical Industries, Ltd.; food additive test grade) as a glycyrrhizin standard, a calibration curve was constructed over the concentration range of 1 to 20 μg/ml, and an assay was carried out.

As a result, the amount of glycyrrhizin in 1 mg/ml of the licorice hydrophobic extract was 4 μg/ml, i.e. the glycyrrhizin content of the extract was 0.4%. Since the glycyrrhizin content is generally not less than 2.5% in licoice powders, not less than 4.5% in aqueous extracts, or not less than 6.0% in hot water extracts, the glycyrrhizin content of the licorice hydrophobic extract was found to be extremely low.

TEST EXAMPLE 1

Visceral Fat Lowering Effect

C57BL/6J mice (female, 10 weeks old) were given a high-fat, high-carbohydrate food (product of Oriental Yeast Co.; Table 1) ad libitum for 4 to 8 weeks to establish dietary obesity. The mice were then divided into groups of 6 to 8 and using a normal food (product of Oriental Yeast Co.; Table 1) as a basal diet, a non-treatment group (control group) and a group given the diet supplemented with the licorice hydrophobic extract obtained in Preparation Example 1 were established. In both groups, the mice had free access to food for 4 weeks. After overnight fasting, the abdomen was opened under ether anesthesia and the mouse was sacrificed by exsanguination from the abdominal aorta. Then, the periuterine fat and perirenal fat were excised and weighed. The sum of periuterine fat weight and perirenal fat weight was recorded as the intra-abdominal fat mass. The data are presented in Table 2.

TABLE 1

| | | High-fat/high-carbohydrate food | Normal food (Modified AIN-93G) |
|---|---|---|---|
| Percent breakdown | Fat | 53% | 22% |
| | Carbohydrate | 27% | 58.5% |
| | Protein | 20% | 19.5% |
| | Total energy | 5,100 kcal/kg | 4,100 kcal/kg |
| Formula | Casein | 25.000% | 20.000% |
| | Cornstarch | 14.869% | 49.948% |
| | Sucrose | 20.000% | 10.000% |
| | Soybean oil | 2.000% | 10.000% |
| | Lard | 14.000% | 0.000% |
| | Beef tallow | 14.000% | 0.000% |
| | Cellulose powder | 5.000% | 5.000% |
| | AIN-93 mineral mix | 3.500% | 3.500% |
| | AIN-93 vitamin mix | 1.000% | 1.000% |
| | Choline bitartrate | 0.250% | 0.250% |
| | tert-Butylhydroquinone | 0.006% | 0.002% |
| | L-cystine | 0.375% | 0.300% |

TABLE 2

| (n = 6/group, Mean ± SD) | Food consumption (g/day/mouse) | Body weight after feeding (g) | Intra-abdominal fat mass/body weight (%) |
|---|---|---|---|
| Non-treatment group (Control group) | 2.92 ± 0.39 | 23.0 ± 1.1 | 1.08 ± 0.24 |
| 0.1% Licorice hydrophobic extract group | 2.81 ± 0.50 | 22.2 ± 0.5 | 0.82 ± 0.15 |

It is apparent from Table 2 that compared with the non-treatment group (control group), the group given the diet supplemented with the licorice hydrophobic extract showed a remarkably smaller intra-abdominal fat mass, although no difference was found in food consumption or in body weight. It is, therefore, clear that the visceral fat accumulated by the intake of a high-fat, high-carbohydrate food was decreased by the intake of a food containing the licorice hydrophobic extract.

TEST EXAMPLE 2

Preventing Effect on Diabetes Mellitus in Type II Diabetic Model Mice-1

Using KK-Ay mice which are model animals presenting with hereditary obesity and developing type II diabetes, the diabetes-preventing effect of the licorice hydrophobic extract prepared in Preparation Example 1 was evaluated. As a positive control, the antidiabetic agent troglitazone was used.

The KK-Ay mice (female, 6 weeks old) were divided into 3 groups (5 per group), and using a normal food (Oriental Yeast Co.; Table 1) as a basal diet, a non-treatment group (control group), a troglitazone group, and a licorice hydrophobic extract group were established. In all groups, the mice had free access to food for 4 weeks. Regarding troglitazone, Noscal Tab. 200 (200 mg of troglitazone in each tablet; Sankyo Co., Ltd.) was pulverized in an agate mortar and added to the normal food at a final concentration of 0.2%. As the licorice hydrophobic extract, the extract prepared in Preparation Example 1 was added to the normal food at a final concentration of 0.15%.

During the feeding period, small samples of blood were taken weekly from the mouse tail vein and the blood glucose was determined with the simple blood glucose test Novo Assist Plus (Novo Nordisk Pharma Ltd.).

At the end of the feeding period, the mice were fasted overnight and the abdomen was opened under ether anesthesia.

The blood was withdrawn from the abdominal aorta and the liver was excised and weighed. In addition, Sogo Ikagaku Kenkyusho Co., Ltd. was entrusted with analyses for serum total cholesterol (T-CHO), triglyceride (TG), free fatty acid (NEFA), GOT, GPT, LAP, cholinesterase (ChoE), total protein (TP-S), albumin (ALB-S), and A/G ratio.

TABLE 3

| | Mouse body weight (g) | | |
|---|---|---|---|
| | Non-treatment group (Control group) | Troglitazone group | Licorice hydrophobic extract group |
| Start | 27.3 ± 1.0 | 28.0 ± 0.8 | 27.7 ± 0.9 |
| 1 week | 33.7 ± 1.3 | 34.5 ± 1.9 | 32.9 ± 0.7 |
| 2 week | 39.2 ± 0.9 | 40.7 ± 3.5 | 39.4 ± 1.7 |

TABLE 3-continued

| | Mouse body weight (g) | | |
|---|---|---|---|
| | Non-treatment group (Control group) | Troglitazone group | Licorice hydrophobic extract group |
| 3 week | 42.1 ± 1.5 | 43.0 ± 5.3 | 41.9 ± 2.1 |
| 4 week | 46.0 ± 1.6 | 48.6 ± 1.6* | 43.9 ± 1.7 |

*($p < 0.05$)

Mouse body weights are shown in Table 3. The mean body weight of mice in the troglitazone group was increased slightly over the non-treatment group (control group) and significantly after 4 weeks. The licorice hydrophobic extract group showed no significant difference from the non-treatment group (control group).

TABLE 4

| | Blood glucose (mg/dl) | | |
|---|---|---|---|
| | Non-treatment group (Control group) | Troglitazone group | Licorice hydrophobic extract group |
| Start | 151 ± 12 | 145 ± 11 | 157 ± 18 |
| 1 week | 391 ± 95 | 217 ± 74** | 358 ± 59 |
| 2 week | 417 ± 71 | 173 ± 40** | 290 ± 78* |
| 3 week | 471 ± 43 | 304 ± 77** | 342 ± 72** |
| 4 week | 441 ± 67 | 246 ± 51** | 272 ± 48** |

*($p < 0.05$),
**($p < 0.01$)

The blood glucose data are presented in Table 4. The blood glucose level at the start of feeding was 145 to 157 mg/dl; none of the groups were hyperglycemic. After 1 week, the blood glucose in the non-treatment group (control group) exceeded 390 mg/dl, indicating the onset of diabetes. In contrast to this non-treatment group (control group), the troglitazone group showed a significant inhibition of blood glucose elevation, indicating that the drug inhibits the elevation of blood glucose. The dosage of troglitazone at this time-point as calculated from mouse body weight and food consumption was about 270 mg/kg/day. On the other hand, the licorice hydrophobic extract group showed a significant inhibition of blood glucose elevation after 2 weeks, indicating that the extract inhibits the elevation of blood glucose. The dosage of the licorice hydrophobic extract at this time-point as calculated from mouse body weight and food consumption was about 190 mg/kg/day.

TABLE 5

| | Non-treatment group (Control group) | Troglitazone group | Licorice hydrophobic extract group |
|---|---|---|---|
| Liver weight (g/100 g body weight) | 4.23 ± 0.27 | 6.84 ± 1.30** | 3.26 ± 0.51 |
| T-CHO (mg/dl) | 161 ± 12 | 163 ± 7 | 131 ± 13** |
| TG (mg/dl) | 121 ± 57 | 39 ± 14* | 82 ± 26 |
| NEFA (µEq/L) | 3299 ± 600 | 1750 ± 302** | 2285 ± 175* |
| GOT (IU/L) | 107 ± 22 | 121 ± 26 | 83 ± 17 |
| GPT (IU/L) | 37.4 ± 13.7 | 70.5 ± 26.2* | 28.2 ± 6.3 |
| LAP (IU/L) | 63.4 ± 8.4 | 60.8 ± 6.1 | 57.4 ± 5.7 |
| ChoE (IU/L) | 145 ± 13 | 153 ± 9 | 145 ± 10 |
| TP-S (g/dl) | 5.00 ± 0.21 | 5.13 ± 0.17 | 4.90 ± 0.10 |
| ALB-S (g/dl) | 2.56 ± 0.13 | 2.50 ± 0.12 | 2.40 ± 0.07 |
| A/G ratio | 1.04 ± 0.05 | 0.98 ± 0.05 | 0.98 ± 0.08 |

*($p < 0.05$),
**($p < 0.01$)

The liver weight data and blood examination data are presented in Table 5. Compared with the non-treatment group (control group), the troglitazone group showed significant decreases in TG and NEFA, indicating the lipid metabolism improving action of the drug. However, the troglitazone group showed a significant gain in liver weight, a significant elevation of GPT, and a 13% elevation, which, however, is not statistically significant, in GOT, suggesting a liver impairment. On the other hand, the licorice hydrophobic extract group showed significant falls in T-CHO and NEFA and a 35% decrease, which, however, is not statistically significant, in TG, indicating the lipid metabolism improving action of the extract. Furthermore, the licorice hydrophobic extract group showed no significant changes in markers of liver function such as liver weight, GOT and GPT, indicating that the extract has no hepatotoxicity.

It was clear from the foregoing results that, like the positive control troglitazone, the licorice hydrophobic extract has both a blood glucose elevation inhibitory action and a lipid metabolism improving action.

PREPARATION EXAMPLE 2

Preparation of a Licorice Hydrophobic Extract-2

Using a glass vessel, 300 g of licorice powder (Kaneka Sun Spice Co., Ltd.) was steeped in 10 volumes of lukewarm water (about 40° C.) and stirred, protected against light, overnight (for about 18 hours). The mixture was then filtered through filter paper (ADVANTEC No. 2) and the residue obtained was dried (about 60° C.) to recover 265 g of an aqueous extraction residue. This residue was steeped in 5 volumes of ethanol and allowed to stand at room temperature, protected against light, for 1 week with occasional stirring. The mixture was filtered through filter paper (ADVANTEC No. 2) twice to remove the powder and recover an extract solution. This extract solution was concentrated under reduced pressure to remove the solvent, whereupon 23.62 g of a licorice hydrophobic extract was obtained.

TEST EXAMPLE 3

Preventing Effect on Diabetes Mellitus in Type II Diabetic Model Mice-2

The preventing effect on diabetes of the licorice hydrophobic extract obtained in Preparation Example 2 was evaluated by the same procedure as used in Test Example 2. In the licorice hydrophobic extract group, the extract prepared in Preparation Example 2 was added to the normal food at a final concentration of 0.2%. As a positive control, the antidiabetic agent pioglitazone was used. As pioglitazone, Actos Tab. 30 (30 mg of pioglitazone in each tablet; Takeda Chemical Industries, Ltd.) was pulverized in an agate mortar and added to the normal food at a final concentration of 0.04% as pioglitazone. For the determination of blood glucose, the simple blood glucose test Glutest Ace (Sanwa Kagaku Kenkyusho Co., Ltd.) was used.

TABLE 6

| | Mouse body weight (g) | | |
|---|---|---|---|
| | Non-treatment group (Control group) | Pioglitazone group | Licorice hydrophobic extract group |
| Start | 27.3 ± 0.3 | 26.9 ± 1.0 | 26.4 ± 0.9 |
| 1 week | 34.5 ± 0.9 | 36.7 ± 1.0 | 34.4 ± 1.9 |
| 2 week | 38.9 ± 1.1 | 39.9 ± 1.2 | 38.8 ± 2.1 |
| 3 week | 42.4 ± 1.5 | 42.9 ± 1.2 | 41.7 ± 1.9 |
| 4 week | 43.5 ± 1.3 | 43.8 ± 1.4 | 43.2 ± 1.9 |

The mouse body weight data are presented in Table 6. The time course of mouse body weight in the pioglitazone group and that in the licorice hydrophobic extract group were both comparable to the time course in the non-treatment group (control group), showing no significant difference.

TABLE 7

| | Blood glucose (mg/dl) | | |
|---|---|---|---|
| | Non-treatment group (Control group) | Pioglitazone group | Licorice hydrophobic extract group |
| Start | 142 ± 12 | 151 ± 9 | 143 ± 8 |
| 1 week | 322 ± 70 | 163 ± 23** | 180 ± 4** |
| 2 week | 427 ± 70 | 182 ± 9** | 257 ± 73** |
| 3 week | 455 ± 66 | 167 ± 18** | 206 ± 26** |
| 4 week | 479 ± 71 | 153 ± 21** | 231 ± 59** |

**($p < 0.01$)

The blood glucose data are presented in Table 7. In the non-treatment group (control group), the blood glucose level was elevated after 1 week, indicating the onset of diabetes. In contrast, the elevation of blood glucose was significantly inhibited in the pioglitazone group, indicating the inhibitory action of the drug on the elevation of blood glucose. The dosage of pioglitazone at this time-point as calculated from mouse body weight and food consumption was about 50 mg/kg/day. The elevation of blood glucose was significantly inhibited in the licorice hydrophobic extract group, too, indicating the inhibitory action of the extract on the elevation of blood glucose. The dosage of the licorice hydrophobic extract at this time-point as calculated from mouse body weight and food consumption was about 260 mg/kg/day.

It is clear from the foregoing results that the licorice hydrophobic extract inhibits the elevation of blood glucose as does the positive control pioglitazone, indicating the preventing effect of the extract on diabetes.

TEST EXAMPLE 4

Ameliorating Effect on Diabetes Mellitus in Type II Diabetic Model Mice

Using KK-Ay mice, the ameliorating effect on diabetes of the licorice hydrophobic extract prepared in Preparation Example 2 was evaluated. As a positive control, the antidiabetic agent pioglitazone was used.

The KK-Ay mice (female, 15 weeks old) were divided into 3 groups (4 per group), and using the normal food as a basal diet, a non-treatment group (control group), a pioglitazone group, and a licorice hydrophobic extract group were established. The mice had free access to food for 7 days. Pioglitazone was added to the normal food at a final concentration of 0.02%. As the licorice hydrophobic extract, the extract prepared in Preparation Example 2 was added to the normal food at a final concentration of 0.2%. For the determination of blood glucose, the simple blood glucose test Glutest Ace (Sanwa Kagaku Kenkyusho Co., Ltd.) was used.

TABLE 8

| | Blood glucose (mg/dl) | | |
|---|---|---|---|
| | Non-treatment group (Control group) | Pioglitazone group | Licorice hydrophobic extract group |
| Start | 391 ± 45 | 378 ± 36 | 389 ± 63 |
| Day 4 | 528 ± 52 | 168 ± 49** | 192 ± 61** |
| Day 7 | 534 ± 44 | 143 ± 16** | 272 ± 61** |

**($p < 0.01$)

The blood glucose data are presented in Table 8. The blood glucose level at the start of feeding was 378 to 391 mg/dl, indicating that the mice in all groups were hyperglycemic. In the non-treatment group (control group), the blood glucose registered about 530 mg/dl on day 4 and day 7, indicating an exacerbation. In contrast, in both the pioglitazone group and the licorice hydrophobic extract group, blood glucose was decreased significantly on both day 4 and day 7, indicating that both the drug and the extract had a hypoglycemic action.

It was clear from the foregoing results that the licorice hydrophobic extract has hypoglycemic action leading to an ameliorative effect of diabetes, just as the positive control pioglitazone.

PREPARATION EXAMPLE 3

Preparation of a Licorice Hydrophobic Extract-3

Using a stainless steel vessel, 1.5 kg of licorice powder (Kaneka Sun Spice Co., Ltd.) was steeped in 10 volumes of water and stirred at room temperature, protected against light, for about 24 hours. The mixture was centrifuged (5,000 g, 20 min.) and the residue obtained was dried (about 55° C.) to give an aqueous extraction residue. This residue was steeped in 5 volumes of ethanol and allowed to stand at room temperature, protected against light, for 1 week with occasional stirring. The mixture was then filtered through filter paper (ADVANTEC No. 2) twice to remove the powder and recover an extract solution. This extract solution was concentrated under reduced pressure to remove the solvent and recover 141.5 g of a licorice hydrophobic extract.

TEST EXAMPLE 5

Efficacy in Spontaneously Hypertensive Rats

Using spontaneously hypertensive rats (SHR) which are model animals of essential hypertension developing hypertension with aging, the efficacy of the licorice hydrophobic extract prepared in Preparation Example 3 was evaluated. As a positive control, enalapril maleate, an antihypertensive agent, was used.

The SHRs (male, 5 week old) were divided into 3 groups (8 per group) to establish a vehicle control group, a licorice hydrophobic extract group, and an enalapril maleate group. The vehicle control group was treated with propylene glycol in doses of 3 ml/kg/day, the licorice hydrophobic extract group with a solution of the licorice hydrophobic extract in propylene glycol in doses of 300 mg/3 ml/kg/day, and the enalapril maleate group with a solution of enalapril maleate in 0.5% methylcellulose (aq. sol.) in doses of 20 mg/10 ml/kg/day, all orally for 3 consecutive weeks. During the period, the mice had free access to food (CRF-1, Oriental Yeast Co.) and water.

On the day immediately preceding the start of treatment and on day 7, day 14, and day 21 of treatment, the blood pressure was measured at the tail artery using a non-invasive automatic hemomanometer (BP-97A, Softron Co., Ltd.). The measurement of blood pressure was performed before each administration of the sample.

TABLE 9

| | Body weight (g) | | |
|---|---|---|---|
| | Vehicle Control group | Licorice hydrophobic extract group | Enalapril maleate group |
| Before start | 76 ± 2.1 | 76 ± 1.7 | 77 ± 1.7 |
| 1 week | 114 ± 2.9 | 118 ± 1.8 | 115 ± 1.0 |
| 2 week | 156 ± 4.1 | 161 ± 2.8 | 151 ± 1.2 |
| 3 week | 192 ± 4.3 | 200 ± 3.1 | 187 ± 1.4 |

The body weights of SHRs are presented in Table 9. The time course of body weight was almost comparable in all groups, showing no significant difference.

TABLE 10

| | Blood pressure (mmHg) | | |
|---|---|---|---|
| | Vehicle Control group | Licorice hydrophobic extract group | Enalapril maleate group |
| Before start | 113 ± 2.2 | 112 ± 2.5 | 111 ± 2.5 |
| Day 7 | 137 ± 4.0 | 125 ± 3.3* | 118 ± 3.2** |
| Day 14 | 156 ± 3.3 | 143 ± 5.2 | 119 ± 3.4** |
| Day 21 | 166 ± 2.9 | 153 ± 2.8** | 134 ± 3.1** |

*($p < 0.05$),
**($p < 0.01$)

The blood pressure data are presented in Table 10. The blood pressure before the start of administration was 111 to 113 mmHg; thus no group showed a hypertensive state. In the vehicle control group, the blood pressure began to rise on day 7, indicating the onset of hypertension. Compared with the vehicle control group, the elevation of blood pressure was inhibited in the licorice hydrophobic extract group, with a significant difference being noted on day 7 and on day 21. In the antihypertensive agent enalapril maleate group, the elevation of blood pressure was significantly inhibited on and after day 7.

It is clear from the foregoing results that the licorice hydrophobic extract is effective in preventing or ameliorating hypertension.

EXAMPLE 1

Preparation of Licorice Hydrophobic Extract-containing Tablets

| | |
|---|---|
| Licorice hydrophobic extract | 45 weight parts |
| Lactose | 35 weight parts |
| Crystalline cellulose | 15 weight parts |
| Sucrose fatty acid ester | 5 weight parts |

According to the above recipe, licorice hydrophobic extract-containing tablets for food/beverage or medical use were manufactured by the established procedure.

EXAMPLE 2

Preparation of Licorice Hydrophobic Extract-containing Soft Capsules

| | |
|---|---|
| Licorice hydrophobic extract | 40 weight parts |
| Sesame oil | 55 weight parts |
| Glycerin fatty acid ester | 5 weight parts |

According to the above recipe, licorice hydrophobic extract-containing soft capsules for food/beverage or medical use were manufactured by the established procedure.

EXAMPLE 3

Preparation of Licorice Hydrophobic Extract-containing Crackers

| | |
|---|---|
| Licorice hydrophobic extract | 1 weight part |
| Soft flour | 120 weight parts |
| Common salt | 1 weight part |
| Baking powder | 2 weight parts |
| Butter | 30 weight parts |
| Water | 40 weight parts |

According to the above recipe, licorice hydrophobic extract-containing crackers were manufactured by the established procedure.

EXAMPLE 4

Preparation of Licorice Hydrophobic Extract-containing Noodles

| | |
|---|---|
| Licorice hydrophobic extract | 1 weight part |
| Hard flour | 100 weight parts |
| Soft flour | 100 weight parts |
| Common salt | 10 weight parts |
| Water | 100 weight parts |

According to the above recipe, licorice hydrophobic extract-containing noodles were manufactured by the established procedure.

EXAMPLE 5

Preparation of a Licorice Hydrophobic Extract-containing Dressing

| | |
|---|---|
| Licorice hydrophobic extract | 10 weight parts |
| Olive oil | 80 weight parts |
| Vinegar | 60 weight parts |
| Common salt | 3 weight parts |
| Pepper | 1 weight part |
| Lemon juice | 5 weight parts |

According to the above recipe, a licorice hydrophobic extract-containing dressing was manufactured by the established procedure.
Turmeric Extract

PREPARATION EXAMPLE 4

Preparation of a Turmeric Extract-1

Using a glass vessel, 400 g of turmeric powder (Kaneka Sun Spice Co., Ltd.) was steeped in 5 volumes of ethanol and allowed to stand at room temperature, protected against light, for 1 week with occasional stirring. The mixture was filtered through filter paper (ADVANTEC No. 2) twice to remove the powder and recover an extract solution. This extract solution was concentrated under reduced pressure to remove the solvent and recover 43.71 g of a turmeric extract.

TEST EXAMPLE 6

Visceral Fat Lowering Effect

C57BL/6J mice (female, 10 weeks old) were given a high-fat, high-carbohydrate food (product of Oriental Yeast Co.; Table 1) ad libitum for 4 to 8 weeks to establish dietary obesity. The mice were then divided into groups of 6 to 8 and using a normal food (product of Oriental Yeast Co.; Table 1) as a basal diet, a non-treatment group (control group) and a group given the diet supplemented with the turmeric extract obtained in Preparation Example 4 were established. In both groups, the mice had free access to food for 4 weeks. After overnight fasting, the abdomen was opened under ether anesthesia and the mouse was sacrificed by exsanguination from the abdominal aorta. Then, the periuterine fat and perirenal fat were excised and weighed. The sum of periuterine fat weight and perirenal fat weight was recorded as the intra-abdominal fat mass. The data are presented in Table 11 and 12.

TABLE 11

| (n = 8/group, Mean ± SD) | Food consumption (g/day/mouse) | Body weight after feeding (g) | Intra-abdominal fat mass/body weight (%) |
|---|---|---|---|
| Non-treatment group (Control group) | 3.17 ± 0.43 | 22.9 ± 1.5 | 1.16 ± 0.73 |
| 1% Turmeric extract group | 2.92 ± 0.62 | 21.7 ± 1.1 | 0.71 ± 0.20 |

TABLE 12

| (n = 6/group, Mean ± SD) | Food consumption (g/day/mouse) | Body weight after feeding (g) | Intra-abdominal fat mass/body weight (%) |
|---|---|---|---|
| Non-treatment group (Control group) | 2.92 ± 0.39 | 23.0 ± 1.1 | 1.08 ± 0.24 |
| 0.5% Turmeric extract group | 2.53 ± 0.59 | 22.6 ± 0.9 | 0.90 ± 0.50 |

It is apparent from Tables 11 and 12 that compared with the non-treatment group (control group), the turmeric extract group showed no difference in food consumption or in body weight but the intra-abdominal fat mass was remarkably decreased in this group. It was clear that the visceral fat accumulated by the intake of the high-fat, high-carbohydrate food was decreased by the intake of the turmeric extract-supplemented food.

PREPARATION EXAMPLE 5

Preparation of a Turmeric Extract-2

Using a glass vessel, 793 g of turmeric powder (Kaneka Sun Spice Co., Ltd.) was steeped in 4,000 ml of ethanol and allowed to stand at room temperature, protected against light, for 1 week with occasional stirring. The mixture was filtered through filter paper (ADVANTEC No. 2) twice to remove the powder and recover an extract solution. This extract solution was concentrated under reduced pressure to remove the solvent and recover 79.48 g of a turmeric extract.

TEST EXAMPLE 7

Efficacy in Type II Diabetic Model Mice

Using KK-Ay mice which are model animals presenting with hereditary obesity and developing type II diabetes, the effect of the turmeric extract was evaluated. As a positive control, the antidiabetic agent pioglitazone was used.

The KK-Ay mice (female, 6 weeks old) were divided into 3 groups (5 per group) and using the normal food (Oriental Yeast Co.; Table 1) as a basal diet, the animals in the non-treatment group (control group), pioglitazone group, and turmeric extract group were fed ad libitum for 4 weeks. As pioglitazone, Actos Tab. 30 (30 mg of pioglitazone in each tablet; Takeda Chemical Industries, Ltd.) was pulverized in an agate mortar and added to the normal food at a final concentration of 0.04% as pioglitazone. As to the turmeric extract, the extract prepared in Preparation Example 5 was added to the normal food at a final concentration of 0.5%.

During the feeding period, small samples of blood were taken weekly from the mouse tail vein and the blood glucose was measured with the simple blood glucose test Glutest Ace (Sanwa Kagaku Kenkyusho Co., Ltd.).

TABLE 13

| | Mouse body weight (g) | | |
|---|---|---|---|
| | Non-treatment group (Control group) | Piogilitazone group | Turmeric extract group |
| Start | 21.3 ± 0.3 | 26.9 ± 1.0 | 27.1 ± 0.8 |
| 1 week | 34.5 ± 0.9 | 36.7 ± 1.0 | 35.3 ± 1.1 |
| 2 week | 38.9 ± 1.1 | 39.9 ± 1.2 | 39.4 ± 1.2 |
| 3 week | 41.0 ± 1.3 | 42.3 ± 1.2 | 41.8 ± 1.3 |
| 4 week | 43.5 ± 1.3 | 43.8 ± 1.4 | 44.4 ± 1.6 |

The body weights of mice are presented in Table 13. Both the pioglitazone group and the turmeric extract group followed nearly the same time courses of body weight as the non-treatment group (control group), showing no significant difference.

TABLE 14

| | Blood glucose (mg/dl) | | |
|---|---|---|---|
| | Non-treatment group (Control group) | Piogiltazone group | Turmeric extract group |
| Start | 142 ± 12 | 151 ± 9 | 142 ± 6 |
| 1 week | 322 ± 70 | 163 ± 23** | 193 ± 28** |
| 2 week | 427 ± 70 | 182 ± 9** | 201 ± 50** |
| 3 week | 455 ± 66 | 166 ± 18** | 244 ± 47** |
| 4 week | 479 ± 71 | 153 ± 21** | 270 ± 37** |

**($p < 0.01$)

The blood glucose data are presented in Table 14. The blood glucose level at the start of feeding was 142 to 151 mg/dl, with none of the groups being hyperglycemic. In the non-treatment group (control group), the blood glucose level was elevated after week 1, indicating the onset of diabetes. In the turmeric extract group, compared with the non-treatment group (control group), the elevation of blood glucose was significantly inhibited as it was true of the antidiabetic pioglitazone group, indicating that the extract has a blood glucose lowering action. The dosage of the turmeric extract at this time-point as calculated from mouse body weight and food consumption was about 670 mg/kg/day. It is clear from the foregoing results that the turmeric extract is effective in preventing or ameliorating diabetes mellitus.

EXAMPLE 6

Preparation of Turmeric Extract-containing Tablets

| | |
|---|---|
| Turmeric extract | 45 weight parts |
| Lactose | 35 weight parts |
| Crystalline cellulose | 15 weight parts |
| Sucrose fatty acid ester | 5 weight parts |

According to the above recipe, turmeric extract-containing tablets for food/beverage or medical use were manufactured by the established procedure.

EXAMPLE 7

Preparation of Turmeric Extract-containing Soft Capsules

| | |
|---|---|
| Turmeric extract | 40 weight parts |
| Sesame oil | 55 weight parts |
| Glycerin fatty acid ester | 5 weight parts |

According to the above recipe, turmeric extract-containing soft capsules for food/beverage or medical use were manufactured by the established procedure.

EXAMPLE 8

Preparation of Turmeric Extract-containing Crackers

| | |
|---|---|
| Turmeric extract | 1 weight part |
| Soft flour | 120 weight parts |
| Common salt | 1 weight part |
| Baking powder | 2 weight parts |
| Butter | 30 weight parts |
| Water | 40 weight parts |

According to the above recipe, turmeric extract-containing crackers were manufactured by the established method.

EXAMPLE 9

Preparation of Turmeric Extract-containing Noodles

| | |
|---|---|
| Turmeric extract | 1 weight part |
| Hard flour | 100 weight parts |
| Soft flour | 100 weight parts |
| Common salt | 10 weight parts |
| Water | 100 weight parts |

According to the above recipe, turmeric extract-containing noodles were manufactured by the established method.

EXAMPLE 10

Preparation of a Turmeric Extract-containing Dressing

| | |
|---|---|
| Turmeric extract | 10 weight parts |
| Olive oil | 80 weight parts |
| Vinegar | 60 weight parts |
| Common salt | 3 weight parts |
| Pepper | 1 weight part |
| Lemon juice | 5 weight parts |

According to the above recipe, a turmeric extract-containing dressing was manufactured by the established procedure.

Clove Extract

PREPARATION EXAMPLE 6

Preparation of a Clove Extract-1

Using a glass vessel, 600 g of clove powder (Kaneka Sun Spice Co., Ltd.) was steeped in 5 volumes of ethyl acetate and allowed to stand at room temperature, protected against light, for 1 week with occasional stirring. The mixture was then filtered through filter paper (ADVANTEC No. 2) twice to remove the powder and recover an extract solution. This extract solution was concentrated under reduced pressure to remove the solvent and recover 47.59 g of a clove extract.

TEST EXAMPLE 8

Visceral Fat Lowering Effect

C57BL/6J mice (female, 10 weeks old) were given a high-fat, high-carbohydrate food (product of Oriental Yeast Co.; Table 1) ad libitum for 4 to 8 weeks to establish dietary obesity. The mice were then divided into groups of 6 to 8 and using a normal food (product of Oriental Yeast Co.; Table 1) as a basal diet, a non-treatment group (control group) and a group given the diet supplemented with the clove extract obtained in Preparation Example 6 were established. In both groups, the mice had free access to food for 4 weeks. After overnight fasting, the abdomen was opened under ether anesthesia and the mouse was sacrificed by exsanguination from the abdominal aorta. Then, the periuterine fat and perirenal fat were excised and weighed. The sum of periuterine fat weight and perirenal fat weight was recorded as the intra-abdominal fat mass. The data are presented in Table 15.

TABLE 15

| (n = 8/group, Mean ± SD) | Food consumption (g/day/mouse) | Body weight after feeding (g) | Intra-abdominal fat mass/body weight (%) |
|---|---|---|---|
| Non-treatment group (Control group) | 3.17 ± 0.43 | 22.9 ± 1.5 | 1.76 ± 0.73 |
| 1% Clove extract group | 2.55 ± 0.53 | 21.7 ± 0.6 | 0.79 ± 0.15 |

It is apparent from Table 15 that compared with the non-treatment group (control group), the clove extract group showed no difference in food consumption or in body weight but the intra-abdominal fat mass was remarkably decreased in this group. It was clear that the visceral fat accumulated by the intake of the high-fat, high-carbohydrate food was decreased by the intake of the clove extract-supplemented food.

PREPARATION EXAMPLE 7

Preparation of a Clove Extract-2

Using a glass vessel, 2 kg of clove powder (Kaneka Sun Spice Co., Ltd.) was steeped in 10 L of ethanol and allowed to stand at room temperature, protected against light, for 1 week with occasional stirring. The mixture was filtered through filter paper (ADVANTEC No. 2) twice to remove the powder and recover an extract solution. This extract solution was concentrated under reduced pressure to remove the solvent and recover 217 g of a clove extract.

TEST EXAMPLE 9

Efficacy in Type II Diabetic Model Mice

Using KK-Ay mice which are model animals presenting with hereditary obesity and developing type II diabetes, the effect of the clove extract was evaluated. As a positive control, the antidiabetic agent pioglitazone was used.

The KK-Ay mice (female, 6 weeks old) were divided into 3 groups (5 per group) and using the normal food (Oriental Yeast Co.; Table 1) as a basal diet, the animals in the non-treatment group (control group), pioglitazone group, and clove extract group were fed ad libitum for 3 weeks. As pioglitazone, Actos Tab. 30 (30 mg of pioglitazone in each tablet; Takeda Chemical Industries, Ltd.) was pulverized in an agate mortar and added to the normal food at a final concentration of 0.02% as pioglitazone. As to the clove extract, the extract prepared in Preparation Example 7 was added to the normal food at a final concentration of 0.5%.

During the feeding period, small samples of blood were taken weekly from the mouse tail vein and the blood glucose was measured with the simple blood glucose test Glutest Ace (Sanwa Kagaku Kenkyusho Co., Ltd.).

TABLE 16

| | Mouse body weight (g) | | |
|---|---|---|---|
| | Non-treatment group (Control group) | Pioglitazone group | Clove extract group |
| Start | 26.7 ± 1.1 | 27.4 ± 0.5 | 27.1 ± 1.1 |
| 1 week | 34.2 ± 2.1 | 35.0 ± 1.1 | 34.7 ± 1.9 |
| 2 week | 39.2 ± 2.0 | 41.0 ± 1.5 | 39.2 ± 1.4 |
| 3 week | 42.7 ± 2.5 | 45.4 ± 1.4 | 42.5 ± 2.1 |

The body weights of mice are presented in Table 16. Both the pioglitazone group and the clove extract group followed nearly the same time courses of body weight as the non-treatment group (control group), showing no significant difference.

TABLE 17

| | Blood glucose (mg/dl) | | |
|---|---|---|---|
| | Non-treatment group (Control group) | Pioglitazone group | Clove extract group |
| Start | 163 ± 14 | 156 ± 16 | 171 ± 14 |
| 1 week | 304 ± 77 | 208 ± 21 | 289 ± 63 |
| 2 week | 457 ± 48 | 192 ± 17** | 274 ± 67** |
| 3 week | 514 ± 60 | 164 ± 16** | 311 ± 90** |

*($p < 0.05$),
**($p < 0.01$)

The blood glucose data are presented in Table 17. The blood glucose level at the start of feeding was 156 to 171 mg/dl, with none of the groups being hyperglycemic. In the non-treatment group (control group), the blood glucose level rose after week 1, indicating the onset of diabetes. In the clove extract group, compared with the non-treatment group (control group), the elevation of blood glucose was significantly inhibited as it was true of the antidiabetic pioglitazone group, indicating that the extract has a blood glucose lowering action. The dosage of the clove extract at this time-point as calculated from mouse body weight and food consumption was about 660 mg/kg/day.

EXAMPLE 11

Preparation of Clove Extract-containing Tablets

| | |
|---|---|
| Clove extract | 45 weight parts |
| Lactose | 35 weight parts |
| Crystalline cellulose | 15 weight parts |
| Sucrose fatty acid ester | 5 weight parts |

According to the above recipe, clove extract-containing tablets for food/beverage or medical use were manufactured by the established procedure.

EXAMPLE 12

Preparation of Clove Extract-containing Soft Capsules

| | |
|---|---|
| Clove extract | 40 weight parts |
| Sesame oil | 55 weight parts |
| Glycerin fatty acid ester | 5 weight parts |

According to the above recipe, clove extract-containing soft capsules for food/beverage or medical use were manufactured by the established procedure.

EXAMPLE 13

Preparation of Clove Extract-containing Crackers

| | |
|---|---|
| Clove extract | 1 weight part |
| Soft flour | 120 weight parts |
| Common salt | 1 weight part |
| Baking powder | 2 weight parts |
| Butter | 30 weight parts |
| Water | 40 weight parts |

According to the above recipe, clove extract-containing crackers were manufactured by the established method.

EXAMPLE 14

Preparation of Clove Extract-containing Noodles

| | |
|---|---|
| Clove extract | 1 weight part |
| Hard flour | 100 weight parts |
| Soft flour | 100 weight parts |
| Common salt | 10 weight parts |
| Water | 100 weight parts |

According to the above recipe, clove extract-containing noodles were manufactured by the established method.

EXAMPLE 15

Preparation of a Clove Extract-containing Dressing

| | |
|---|---|
| Clove extract | 10 weight parts |
| Olive oil | 80 weight parts |
| Vinegar | 60 weight parts |
| Common salt | 3 weight parts |
| Pepper | 1 weight part |
| Lemon juice | 5 weight parts |

According to the above recipe, a clove extract-containing dressing was manufactured by the established method.
Cinnamon extract

PREPARATION EXAMPLE 8

Preparation of a Cinnamon Extract

Using a glass vessel, 1,000 g of cinnamon powder (Kaneka Sun Spice Co., Ltd.) was steeped in 5 volumes of ethyl acetate and allowed to stand at room temperature, protected against light, for 1 week with occasional stirring. The mixture was then filtered through filter paper (ADVANTEC No. 2) twice to remove the powder and recover an extract solution. This extract solution was concentrated under reduced pressure to remove the solvent and recover 59.57 g of a cinnamon extract.

TEST EXAMPLE 10

Visceral Fat Lowering Effect

C57BL/6J mice (female, 10 weeks old) were given a high-fat, high-carbohydrate food (product of Oriental Yeast Co.; Table 1) ad libitum for 4 to 8 weeks to establish dietary obesity. The mice were then divided into groups of 6 to 8 and using a normal food (product of Oriental Yeast Co.; Table 1) as a basal diet, a non-treatment group (control group) and a group given the diet supplemented with the cinnamon extract obtained in Preparation Example 8 were established. In both groups, the mice had free access to food for 4 weeks. After overnight fasting, the abdomen was opened under ether anesthesia and the mouse was sacrificed by exsanguination from the abdominal aorta. Then, the periuterine fat and perirenal fat were excised and weighed. The sum of periuterine fat weight and perirenal fat weight was recorded as the intra-abdominal fat mass. The data are presented in Table 18.

TABLE 18

| (n = 8/group, Mean ± SD) | Food consumption (g/day/mouse) | Body weight after feeding (g) | Intra-abdominal fat mass/body weight (%) |
|---|---|---|---|
| Non-treatment group (Control group) | 3.17 ± 0.43 | 22.9 ± 1.5 | 1.76 ± 0.73 |
| 1% Cinnamon extract group | 2.61 ± 0.38 | 21.5 ± 1.0 | 1.00 ± 0.27 |

It is apparent from Table 18 that compared with the non-treatment group (control group), the cinnamon extract group showed no difference in food consumption or in body weight but the intra-abdominal fat mass was remarkably decreased in this group. It was clear that the visceral fat accumulated by the intake of the high-fat, high-carbohydrate food was decreased by the intake of the cinnamon extract-supplemented food.

EXAMPLE 16

Preparation of Cinnamon Extract-containing Tablets

| | |
|---|---|
| Cinnamon extract | 45 weight parts |
| Lactose | 35 weight parts |
| Crystalline cellulose | 15 weight parts |
| Sucrose fatty acid ester | 5 weight parts |

According to the above recipe, cinnamon extract-containing tablets for food/beverage or medical use were manufactured by the established procedure.

INDUSTRIAL APPLICABILITY

The present invention, constituted as above, provides a composition for preventing or ameliorating multiple risk factor syndrome involving visceral fat-type obesity, diabetes mellitus, hyperlipemia, and hypertension. Intake of the composition of the invention results in reductions in accumulated visceral fat and, hence, leads to preventing or ameliorating lifestyle-related diseases arising from accumulation of visceral fat, such as obesity, diabetes mellitus, hyperlipemia, and hypertension.

What is claimed is:

1. A method for ameliorating multiple risk factor syndrome including visceral fat-type obesity, which comprises administrating to a subject suffering from multiple risk factor syndrome and visceral fat-type obesity wherein the multiple risk factor syndrome is a syndrome which co-develops visceral fat-type obesity and at least one member selected from the group consisting of diabetes mellitus, hyperlipemia and hypertension, a composition comprising a licorice hydrophobic extract, wherein the glycyrrhizin content in the licorice hydrophobic extract is not more than 0.4%; and wherein the licorice hydrophobic extract is an extract obtained by extracting out the licorice with ethyl acetate and/or ethanol or an extract from which the ethyl acetate and/or ethanol extractant solvent has been removed.

2. The method according to claim 1, wherein the composition is orally administered to the subject.

3. The method according to claim 1, wherein the licorice hydrophobic extract is obtained by extracting out the hydrophilic component of licorice with water or an alkaline aqueous solution in advance and extracting the licorice residue, either as it is or after drying, with said solvent ethyl acetate and/or ethanol.

4. The method according to claim 1, wherein the composition is a food or beverage.

5. The method according to claim 1, wherein the composition is a medicinal agent.

6. The method according to claim 1, wherein the subject is a human being.

7. The method according to claim 1, wherein the subject is a domestic or pet animal.

8. The method according to claim 1, wherein the composition is a cosmetic.

9. A method for ameliorating visceral fat-type obesity, which comprises administrating to a subject suffering from visceral fat-type obesity, a composition comprising a licorice hydrophobic extract, wherein the glycyrrhizin content in the licorice hydrophobic extract is not more than 0.4%; and wherein the licorice hydrophobic extract is an extract obtained by extracting out the licorice with ethyl acetate and/or ethanol or an extract from which the ethyl acetate and/or ethanol extractant solvent has been removed.

10. The method according to claim 9, wherein the composition is orally administered to the subject.

11. The method according to claim 9, wherein the licorice hydrophobic extract is obtained by extracting out the hydrophilic component of licorice with water or an alkaline aqueous solution in advance and extracting the licorice residue, either as it is or after drying, with said solvent ethyl acetate and/or ethanol.

12. The method according to claim 9, wherein the composition is a food or beverage.

13. The method according to claim 9, wherein the composition is a medicinal agent.

14. The method according to claim 9, wherein the subject is a human being.

15. The method according to claim 9, wherein the subject is a domestic or pet animal.

16. The method according to claim 9, wherein the composition is a cosmetic.

* * * * *